United States Patent
Thompson et al.

(10) Patent No.: US 7,365,053 B2
(45) Date of Patent: Apr. 29, 2008

(54) SELECTIVE N-ACYLATION OF A82846 GLYGOPEPTIDES ANALOGS

(75) Inventors: Richard Craig Thompson, Frankfort, IN (US); Stephen Charles Wilkie, Indianapolis, IN (US); Mark James Zweifel, Mooresville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 481 days.

(21) Appl. No.: 10/203,533

(22) PCT Filed: Feb. 12, 2001

(86) PCT No.: PCT/US01/04540

§ 371 (c)(1),
(2), (4) Date: Feb. 6, 2003

(87) PCT Pub. No.: WO01/58933

PCT Pub. Date: Aug. 16, 2001

(65) Prior Publication Data

US 2007/0219123 A1    Sep. 20, 2007

Related U.S. Application Data

(60) Provisional application No. 60/181,683, filed on Feb. 11, 2000.

(51) Int. Cl.
*A61K 38/00* (2006.01)

(52) U.S. Cl. .......................................................... 514/8
(58) Field of Classification Search .................... None
See application file for complete search history.

(56) References Cited

U.S. PATENT DOCUMENTS

| 4,639,433 | A |   | 1/1987  | Hunt et al. |
|-----------|---|---|---------|-------------|
| 4,643,987 | A |   | 2/1987  | Nagarajan et al. |
| 4,698,327 | A |   | 10/1987 | Nagarajan et al. |
| 5,591,714 | A | * | 1/1997  | Nagarajan et al. .............. 514/9 |
| 5,840,684 | A |   | 11/1998 | Cooper et al. |

FOREIGN PATENT DOCUMENTS

| EP | 0 435 503 | 12/1990 |
|----|-----------|---------|
| WO | 99/56760  | 11/1999 |

OTHER PUBLICATIONS

Cooper et al., *J. Antiobiotics*, 49:6, 575-581 (1996) Reductive Alkylation of Glycopeptide Antibiotics: Synthesis and Antibacterial Activity.
Nagarajan et al., *J. Antiobiotics*, 41:10, 1430-1438 (1988) Synthesis and antibacterial activity of N-acyl vancomycins.
International Search Report PCT/US 01/04540, dtd. Oct. 24, 2001.

* cited by examiner

*Primary Examiner*—Cecilia J. Tsang
*Assistant Examiner*—Roy Teller

(57) ABSTRACT

The present invention provides a process for selectively acylating an A82846A, A82846B, A82846C or PA-42867-A glycopeptide at the N1, N2 or N3 positions and the monoacylated compounds prepared therefrom.

17 Claims, No Drawings

SELECTIVE N-ACYLATION OF A82846 GLYGOPEPTIDES ANALOGS

CROSS-REFERENCE TO RELATED APPLICATIONS

This application is a National Stage application under 35 U.S.C. 371 of PCT/US01/04540, filed 12 Feb. 2001, and published in English on 16 Aug. 2001 as WO 01/58933, and claims benefit of U.S. Provisional Application 60/181,683, filed 11 Feb. 2000.

FIELD OF INVENTION

The present invention relates to a process for selectively N-acylating a glycopeptide, in particular, A82846A, A82846B, A82846C and PA-42867A.

BACKGROUND

The emergence of *enterococci* resistant to Vancomycin has been increasing over the past decade. Given that vancomycin is the last defense against many Gram-positive organisms, including methicillin-resistant *staphylococcus aureus* (MRSA), there is an urgency for new antibiotics. In recent years, research has focused on glycopeptides that are structurally similar to vancomycin in the search for new antibiotics that may be active against these resistant strains, including Vancomycin-Resistant Enterococci (VRE). A82846 glycopeptide analogs have been shown to be some of the most active glycopeptides against a broad range of multi-drug resistant organisms. (see, e.g., U.S. Pat. Nos. 5,591,714 and 5,840,684; and Cooper, R. D. G., N. J. Snyder, M. J. Zweifel, M. A. Staszak, S. C. Wilkie, T. I. Nicas, D. L. Mullen, T. F. Butler, M. J. Rodriguez, B. E. Huff, and R. C. Thompson, "Reductive Alkylation of Glycopeptide Antibiotics: Synthesis and Antibacterial Activity," *J. Antibiotics*, 49 (6) 575-581 (1996)).

The natural A82846 analogs and Vancomycin are from the same general class of glycopeptides and have very similar structures. The major difference involves the presence of a 4-epi-vancosaminyl sugar at the benzylic hydroxyl of the sixth amino acid in the A82846 analogs and the different stereochemistry at the 4-position of the amino sugar in the disaccharide of the A82846 analogs as opposed to vancomycin. In general, these changes result in an increase in antibiotic activity. A82846 analogs have been shown to be more active than vancomycin against *enterococci* and equally as active against most *staphylococcus* strains.

Synthetic modifications of glycopeptide antibiotics can be difficult due to their complex structures and their insolubility in reaction solvents. There are many conditions disclosed in the literature for amino acid acylations, a number of which have been successfully used for the acylation of vancomycin. For example, U.S. Pat. Nos. 4,639,433; 4,643,987; and 4,698,327 describe the preparation of N-acyl derivatives of the glycopeptides vancomycin, A51568A, A51568B, M43A and M43D. (See also Nagarajan, R., A. A. Schabel, J. L. Occolowitz, F. T. Counter, and J. L. Ott, "Synthesis and antibacterial activity of N-acyl vancomycins," *J. Antibiotics*, 41 (10), 1430-1438 (1988).) However, most of these conditions do not result in acylated products of A82846B. Unlike vancomycin, there are 3 separate sites of acylation in the A82846 analogs: the 2 saccharide amino groups (N1 and N2) and the N-terminal N-methyl leucine nitrogen (N3), which can result in 7 different products, 3 mono-, 3 di-, and 1 tri-substituted products.

U.S. Pat. No. 5,591,714 describes the acylation of A82846A, A82846B, A82846C, and PA-42967-A. However, the conditions described therein do not provide guidance on how to selectively acylate either the N1 and N2 positions or the N3 position. Therefore, there is a need for an improved method for selectively acylating the A82846 glycopeptide analogs.

SUMMARY

The present invention provides methods for selectively acylating the N1 or N2 positions of an A82846 glycopeptide such as A82846A, A82846B, A82846C or PA-42867-A by acylating the parent glycopeptide with an activated ester such as N-acyl-hydroxysuccinimide or N-acyl-hydroxyphthalimide in dimethylsulfoxide (DMSO). Alternatively, the N3 position is selectively acylated when the parent glycopeptide is acylated with an activated ester such as N-acyl-hydroxysuccinimide or N-acyl-hydroxyphthalimide in aqueous methanol. The invention also provides the N-monoacylated glycopeptide compounds resulting therefrom.

Furthermore, the invention provides the following: pharmaceutical compositions of the N-monoacylated glycopeptides described herein; use of the monoacylated glycopeptides for treating a staphylococcal infection; use of the monoacylated glycopeptides for the manufacture of a medicament for treating a staphylococcal infection; and a method of controlling the growth of a microorganism susceptible to the antimicrobial activity of the monoacylated glycopeptide by providing to the locus where the microorganism is present (or contacting the microorganism) with an effective amount of the glycopeptide.

DETAILED DESCRIPTION

Definitions

As used above, and throughout the description of the invention, the following terms, unless otherwise indicated, shall be understood to have the following meanings:—

Parent glycopeptides A82846A, A82846B, A82846C and PA-42867-A are represented by the following structure having the corresponding identifications of X and Y indicated in the listings immediately following the structure.

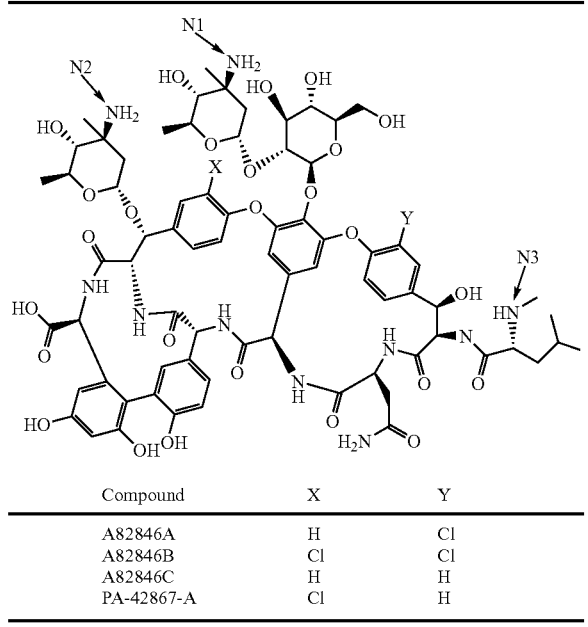

| Compound | X | Y |
|---|---|---|
| A82846A | H | Cl |
| A82846B | Cl | Cl |
| A82846C | H | H |
| PA-42867-A | Cl | H |

"Acid bioisostere" means a group which has chemical and physical similarities producing broadly similar biological properties to a carboxy group (see Lipinski, Annual Reports in Medicinal Chemistry, "Bioisosterism In Drug Design" 21, 283 (1986); Yun, Hwahak Sekye, "Application of Bioisosterism To New Drug Design" 33, 576-579, (1993); Zhao, Huaxue Tongbao, "Bioisosteric Replacement And Development Of Lead Compounds In Drug Design" 34-38, (1995); Graham, Theochem, "Theoretical Studies Applied To Drug Design:ab initio Electronic Distributions In Bioisosteres" 343, 105-109, (1995)). Examples of suitable acid bioisosteres include: —C(O)—NHOH, —C(O)—CH$_2$OH, —C(O)—CH$_2$SH, —C(O)—NH—CN, sulpho, phosphono, alkylsulphonylcarbamoyl, tetrazolyl, arylsulphonylcarbamoyl, N-methoxycarbamoyl, heteroarylsulphonylcarbamoyl, 3-hydroxy-3-cyclobutene-1,2-dione, 3,5-dioxo-1,2,4-oxadiazolidinyl or hydroxyheteroaryl such as 3-hydroxyisoxazolyl and 3-hydroxy-1-methylpyrazolyl.

"Acidic functional group" means a moiety bearing an acidic hydrogen. Exemplary acid functional groups include carboxyl (—C(O)OH), acid bioisostere, imidazolyl, mercapto and an appropriate hydroxy such as an aromatic hydroxy, e.g., hydroxyphenyl.

"Acid protecting group" means an easily removable group that is known in the art to protect an acidic hydrogen of a carboxyl group against undesirable reaction during synthetic procedures, e.g., to block or protect the acid functionality while the reactions involving other functional sites of the compound are carried out, and to be selectively removable. Such acid protecting groups are well known to those skilled in the art, having been extensively used in the protection of carboxyl groups, as described in U.S. Pat. Nos. 3,840,556 and 3,719,667, the disclosures of which are hereby incorporated herein by reference. For suitable acid protecting groups, see T. W. Green and P. G. M. Wuts in "Protective Groups in Organic Chemistry" John Wiley and Sons, 1991. Acid protecting group also includes hydrogenation labile acid protecting group as defined herein. Examples of acid protecting groups include esters such as substituted and unsubstituted $C_1$ to $C_8$ lower alkyl, e.g., methyl, ethyl, t-butyl, methoxymethyl, methylthiomethyl, 2,2,2-trichloroethyl and the like, tetrahydropyranyl, substituted and unsubstituted phenylalkyl such as benzyl and substituted derivatives thereof such as alkoxybenzyl or nitrobenzyl groups and the like, cinnamyl, dialkylaminoalkyl, e.g., dimethylaminoethyl and the like, trimethylsilyl, substituted and unsubstituted amides and hydrazides, e.g., amides and hydrazides of N,N-dimethylamine, 7-nitroindole, hydrazine, N-phenylhydrazine and the like, acyloxyalkyl groups such as pivaloyloxymethyl or propionyloxymethyl and the like, aroyloxyalkyl such as benzoyloxyethyl and the like, alkoxycarbonylalkyl such as methoxycarbonylmethyl, cyclohexyloxycarbonylmethyl and the like, alkoxycarbonyloxyalkyl such as t-butyloxycarbonyloxymethyl and the like, alkoxycarbonylaminoalkyl such as t-butyloxycarbonylaminomethyl and the like, alkylaminocarbonylaminoalkyl, such as methylaminocarbonylaminomethyl and the like, acylaminoalkyl such as acetylaminomethyl and the like, heterocyclylcarbonyloxyalkyl such as 4-methylpiperazinyl-carbonyloxymethyl and the like, dialkylaminocarbonylalkyl such as dimethylaminocarbonyl-methyl and the like, (5-(lower alkyl)-2-oxo-1,3-dioxolen-4-yl)alkyl such as (5-t-butyl-2-oxo-1,3-dioxolen-4-yl)methyl and the like, and (5-phenyl-2-oxo-1,3-dioxolen-4-yl)alkyl such as (5-phenyl-2-oxo-1,3-dioxolen-4-yl)methyl and the like.

"Acid labile amine protecting group" means an amine protecting group as defined herein which is readily removed by treatment with acid while remaining relatively stable to other reagents. An exemplary acid labile amine protecting group is BOC.

"Acyl" means an H—CO—, (aliphatic or cyclyl)-CO—, or (aromatic or heteroaromatic)-CO— group wherein the aliphatic, cyclyl, aromatic, or heteroaromatic group is as herein described. Preferred acyls contain a lower alkyl; more preferred acyls include 4-phenylbenzoyl, 4-(4'-chlorophenyl)benzoyl, 4-octyloxybenzoyl, octanoyl, and 8-phenyloctanoyl. Exemplary acyl groups include formyl, acetyl, propanoyl, 2-methylpropanoyl, butanoyl, palmitoyl, acryloyl, propynoyl and cyclohexylcarbonyl.

"Aliphatic" means alkyl, alkenyl or alkynyl as defined herein.

"Aliphatic group substituents" mean substituents attached to a aliphatic group as defined herein inclusive of aryl, heteroaryl, hydroxy, alkoxy, cyclyloxy, aryloxy, heteroaryloxy, acyl or its thioxo analogue, cyclylcarbonyl or its thioxo analogue, aroyl or its thioxo analogue, heteroaroyl or its thioxo analogue, acyloxy, cyclylcarbonyloxy, aroyloxy, heteroaroyloxy, halo, nitro, cyano, carboxy (acid), acid biostere, alkoxycarbonyl, cyclyloxycarbonyl, aryloxycarbonyl, heteroaryloxycarbonyl, alkylsulfonyl, cyclylsulfonyl, arylsulfonyl, heteroarylsulfonyl, alkylsulfinyl, cyclylsulfinyl, arylsulfinyl, heteroarylsulfinyl, alkylthio, cyclylthio, arylthio, heteroarylthio, cyclyl, aryldiazo, heteroaryldiazo, thiol, methylene (H$_2$C=), oxo (O=), thioxo (S=), $Y^1Y^2N$—, $Y^1Y^2NC(O)$—, $Y^1Y^2NC(O)O$—, $Y^1Y^2NC(O)NY^3$— or $Y^1Y^2NSO_2$—, wherein $Y^1$, $Y^2$ and $Y^3$ are independently hydrogen, optionally substituted alkyl, optionally substituted aryl or optionally substituted heteroaryl, or for where the substituent is $Y^1Y^2N$—, then one of $Y^1$ and $Y^2$ may be acyl, cyclylcarbonyl, aroyl, heteroaroyl, alkoxycarbonyl, cyclyloxycarbonyl, aryloxycarbonyl or heteroaryloxycarbonyl, as defined herein and the other of $Y^1$ and Y is as defined previously, or for where the substituent is $Y^1Y^2NC(O)$—, $Y^1Y^2NC(O)O$—, $Y^1Y^2NC(O)NY^3$— or $Y^1Y^2NSO_2$—, $Y^1$ and $Y^2$ may also be taken together with the N atom through which $Y^1$ and $Y^2$ are linked to form a 4 to 7 membered azaheterocyclyl or azaheterocyclenyl. Acidic/amide aliphatic group substituents are carboxy (acid), acid biostere and $Y^1Y^2NCO$—. Non-acidic polar aliphatic group substituents are hydroxy, oxo (O=), thioxo (S=), acyl or its thioxo analogue, cyclylcarbonyl or its thioxo analogue, aroyl or its thioxo analogue, heteroaroyl or its thioxo analogue, alkoxycarbonyl, cyclyloxycarbonyl, aryloxycarbonyl, heteroaryloxycarbonyl, acyloxy, cyclylcarbonyloxy, aroyloxy, heteroaroyloxy, alkylsulfonyl, cyclylsulfonyl, arylsulfonyl, heteroarylsulfonyl, alkylsulfinyl, cyclylsulfinyl, arylsulfinyl, heteroarylsulfinyl, thiol, $Y^1Y^2N$—, $Y^1Y^2NC(O)$—, $Y^1Y^2NC(O)O$—, $Y^1Y^2NC(O)NY^3$— or $Y^1Y^2NSO_2$—. Examples of aliphatic groups bearing an aliphatic group substituent include the following: methoxymethoxy, methoxyethoxy, ethoxyethoxy, (methoxy-, benzyloxy-, phenoxy-, or ethoxy-)carbonyl(methyl or ethyl), benzyloxycarbonyl, pyridylmethyloxycarbonylmethyl, methoxyethyl, ethoxymethyl, n-butoxymethyl, cyclopentylmethyloxyethyl, phenoxypropyl, phenoxyallyl, trifluoromethyl, cyclopropylmethyl, cyclopentylmethyl, carboxy(methyl or ethyl), 2-phenethenyl, benzyloxy, 1- or 2-naphthyl-methoxy, 4-pyridylmethyloxy, benzyloxyethyl, 3-benzyloxyallyl, 4-pyridylmethyloxyethyl, 4-pyridylmethyloxyallyl, benzyl, 2-phenethyl, naphthylmethyl, styryl, 4-phenyl-1,3-pentadienyl, phenylpropynyl, 3-phenylbut-2-ynyl, pyrid-3-ylacetylenyl and quinolin-3-ylacetylenyl, 4-pyridylethynyl, 4-pyridylvinyl, thienylethenyl, pyridylethenyl, imidazolylethenyl, pyrazinylethenyl, pyridylpentenyl, pyridylhexenyl and pyridylheptenyl, thienylmethyl, pyridylmethyl, imidazolylmethyl, pyrazinylmethyl, tetrahydropyranylmethyl and tetrahydropyranylmethyloxymethyl "Alkenoyl" means an alkenyl-CO— group wherein alkenyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain that may be straight or branched. The alkenyl group is optionally substituted with one or more "aliphatic group substituents" which may be the same or different, and are as described herein. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenyloxy" means an alkenyl-O— group wherein the alkenyl group is as herein described. Exemplary alkenyloxy groups include allyloxy or 3-butenyloxy.

"Alkoxy" means an alkyl-O— group wherein the alkyl group is as herein described. Exemplary alkoxy groups include methoxy, ethoxy, n-propoxy, i-propoxy, n-butoxy and heptoxy.

"Alkoxycarbonyl" means an alkyl-O—CO— group, wherein the alkyl group is as herein defined. Exemplary alkoxycarbonyl groups include methoxycarbonyl, ethoxycarbonyl, or t-butyloxycarbonyl.

"Alkyl" means an aliphatic hydrocarbon group which may be straight or branched having about 1 to about 20 carbon atoms in the chain. Preferred alkyl groups have 1 to about 12 carbon atoms in the chain, more preferred is lower alkyl as defined herein. Branched means that one or more lower alkyl groups such as methyl, ethyl or propyl are attached to a linear alkyl chain. "Lower alkyl" means about 1 to about 4 carbon atoms in the chain that may be straight or branched. The alkyl group is optionally substituted with one or more "aliphatic group substituents" which may be the same or different, and are as described herein.

"Alkylsulfinyl" means an alkyl-SO— group wherein the alkyl group is as defined above. Preferred groups are those wherein the alkyl group is lower alkyl.

"Alkylsulfonyl" means an alkyl-$SO_2$-group wherein the alkyl group is as defined above. Preferred groups are those wherein the alkyl group is lower alkyl.

"Alkylsulphonylcarbamoyl" means an alkyl-$SO_2$—NH—C(=O)— group wherein the alkyl group is as herein described. Preferred alkylsulphonylcarbamoyl groups are those wherein the alkyl group is $C_{1-4}$ alkyl.

"Alkylthio" means an alkyl-S— group wherein the alkyl group is as herein described. Exemplary alkylthio groups include methylthio, ethylthio, i-propylthio and heptylthio.

"Alkynoyl" means an alkynyl-CO— group wherein alkynyl is as defined herein.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about 4 carbon atoms in the chain. Branched means that one or more lower alkyl groups such as methyl, ethyl or propyl are attached to a linear alkynyl chain. "Lower alkynyl" means about 2 to about 4 carbon atoms in the chain that may be straight or branched. The alkynyl group is optionally substituted with one or more "aliphatic group substituents' which may be the same or different, and are as described herein. Exemplary alkynyl groups include ethynyl, propynyl, n-butynyl, 2-butynyl, 3-methylbutynyl, n-pentynyl, heptynyl, octynyl and decynyl.

"Alkynyloxy" means an alkynyl-O— group wherein the alkynyl group is as herein described. Exemplary alkynyloxy groups include propynyloxy or 3-butynyloxy.

"Amine protecting group" means an easily removable group that is known in the art to protect an amino group against undesirable reaction during synthetic procedures and to be selectively removable. The use of amine protecting groups is well known in the art for protecting groups against undesirable reactions during a synthetic procedure and many such protecting groups are known, for example, T. H. Greene and P. G. M. Wuts, Protective Groups in Organic Synthesis, 2nd edition, John Wiley & Sons, New York (1991), incorporated herein by reference. Amine protecting group also includes "acid labile amine protecting group" and "hydrogenation labile amine protecting group". Particular amine protecting groups are acyl, including formyl, acetyl, chloroacetyl, trichloroacetyl, o-nitrophenylacetyl, o-nitrophenoxy-acetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxy-carbonyl, 9-fluorenylmethoxycarbonyl, 2,2,2-trifluoroethoxycarbonyl, 2-trimethylsilylethoxy-carbonyl, vinyloxycarbonyl, allyloxycarbonyl, t-butyloxycarbonyl (BOC), 1,1-dimethyl-propynyloxycarbonyl, benzyloxycarbonyl (CBZ), p-nitrobenzyloxycarbonyl, 2,4-dichloro-benzyloxycarbonyl, and the like.

"Aromatic group" means aryl or heteroaryl as defined herein. Exemplary aromatic groups include phenyl, halo substituted phenyl and azaheteroaryl.

"Aroyl" means an aryl-CO— group wherein the aryl group is as herein described. Exemplary groups include benzoyl and 1- and 2-naphthoyl.

"Aryl" means an aromatic monocyclic or multicyclic ring system of about 6 to about 14 carbon atoms, preferably of about 6 to about 10 carbon atoms. Encompassed by aryl are fused arylcycloalkenyl, fused arylcycloalkyl, fused arylheterocyclenyl and fused arylheterocyclyl as defined herein when bonded through the aryl moiety thereof. The aryl is optionally substituted with one or more "ring group substituents" which may be the same or different, and are as defined herein. Exemplary aryl groups include phenyl or naphthyl, or phenyl substituted or naphthyl substituted. Preferred aryl groups are phenyl and biphenyl.

"Aryldiazo" means an aryl-diazo-group wherein the aryl and diazo groups are as defined herein.

"Arylene" means an optionally substituted 1,2-, 1,3-, 1,4-, bivalent aryl group, wherein the aryl group is as defined herein. Exemplary arylene groups include optionally substituted phenylene, naphthylene and indanylene. A particular arylene is optionally substituted phenylene. Suitable substituents include one or more "ring group substituents" as defined above.

"Aryloxy" means an aryl-O— group wherein the aryl group is as defined herein. Exemplary groups include phenoxy and 2-naphthyloxy.

"Aryloxycarbonyl" means an aryl-O—CO— group wherein the aryl group is as defined herein. Exemplary aryloxycarbonyl groups include phenoxycarbonyl and naphthoxycarbonyl.

"Arylsulfonyl" means an aryl-$SO_2$— group wherein the aryl group is as defined herein.

"Arylsulphonylcarbamoyl" means an aryl-SO$_2$—NH—C(=O)— group wherein the aryl group is as herein described. An exemplary arylsulphonylcarbamoyl group is phenylsulphonylcarbamoyl.

"Arylsulfinyl" means an aryl-SO— group wherein the aryl group is as defined herein.

"Arylthio" means an aryl-S— group wherein the aryl group is as herein described. Exemplary arylthio groups include phenylthio and naphthylthio.

"Carboxy" means an HO(O)C— (carboxylic acid) group.

"Cycloalkenyl" means a non-aromatic mono- or multicyclic ring system of about 3 to about 10 carbon atoms, preferably of about 5 to about 10 carbon atoms, and which contains at least one carbon-carbon double bond. Encompassed by cycloalkenyl are fused arylcycloalkenyl and fused heteroarylcycloalkenyl as defined herein when bonded through the cycloalkenyl moiety thereof. Preferred ring sizes of rings of the ring system include about 5 to about 6 ring atoms; and such preferred ring sizes are also referred to as "lower". The cycloalkenyl is optionally substituted with one or more "ring group substituents" which may be the same or different, and are as defined herein. Exemplary monocyclic cycloalkenyl include cyclopentenyl, cyclohexenyl, cycloheptenyl, and the like. An exemplary multicyclic cycloalkenyl is norbornylenyl.

"Cycloalkyl" means a non-aromatic mono- or multicyclic ring system of about 3 to about 10 carbon atoms, preferably of about 5 to about 10 carbon atoms. Preferred ring sizes of rings of the ring system include about 5 to about 6 ring atoms; and such preferred ring sizes are also referred to as "lower". Encompassed by cycloalkyl are fused arylcycloalkyl and fused heteroarylcycloalkyl as defined herein when bonded through the cycloalkyl moiety thereof. The cycloalkyl is optionally substituted with one or more "ring group substituents" which may be the same or different, and are as defined herein. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

"Cycloalkylene" means a bivalent, saturated carbocyclic group having about 4 to about 8 carbon atoms. Exemplary cycloalkylene groups include 1,2-, 1,3-, or 1,4-cis or trans-cyclohexanylene.

"Cyclic" means cycloalkyl, cycloalkenyl, heterocyclyl or heterocyclenyl as defined herein. The term "lower" as used in connection with the term cyclic is same as noted herein regarding the cycloalkyl, cycloalkenyl, heterocyclyl or heterocyclenyl.

"Cyclyloxy" means a cyclyl-O— group wherein the cyclyl group is as herein described. Exemplary cycloalkoxy groups include cyclopentyloxy, cyclohexyloxy, quinuclidyloxy, pentamethylenesulfideoxy, tetrahydropyranyloxy, tetrahydrothiophenyloxy, pyrrolidinyloxy, tetrahydrofuranyloxy or 7-oxabicyclo[2.2.1]heptanyloxy, hydroxytetrahydropyranyloxy and hydroxy-7-oxabicyclo[2.2.1]heptanyloxy.

"Cyclylsulfinyl" means a cyclyl-S(O)— group wherein the cyclyl group is as herein described.

"Cyclylsulfonyl" means a cyclyl-S(O)$_2$— group wherein the cyclyl group is as herein described.

"Cyclylthio" means a cyclyl-S— group wherein the cyclyl group is as herein described.

"Diazo" means a bivalent —N=N— radical.

"Effective amount" is means an amount of a compound/composition according to the present invention effective in producing the desired therapeutic effect.

"Fused arylcycloalkenyl" means a fused aryl and cycloalkenyl as defined herein. Preferred fused arylcycloalkenyls are those wherein the aryl thereof is phenyl and the cycloalkenyl consists of about 5 to about 6 ring atoms. A fused arylcycloalkenyl as a variable may be bonded through any atom of the ring system thereof capable of such. The fused arylcycloalkenyl may be optionally substituted by one or more ring group substituent, wherein the "ring group substituent" is as defined herein. Exemplary fused arylcycloalkenyl include 1,2-dihydronaphthylene, indene, and the like.

"Fused arylcycloalkyl" means a fused aryl and cycloalkyl as defined herein. Preferred fused arylcycloalkyls are those wherein the aryl thereof is phenyl and the cycloalkyl consists of about 5 to about 6 ring atoms. A fused arylcycloalkyl as a variable may be bonded through any atom of the ring system thereof capable of such. The fused arylcycloalkyl may be optionally substituted by one or more ring group substituent, wherein the "ring group substituent" is as defined herein. Exemplary fused arylcycloalkyl includes 1,2,3,4-tetrahydro-naphthylene, and the like.

"Fused arylheterocyclenyl" means a fused aryl and heterocyclenyl as defined herein. Preferred fused arylheterocyclenyls are those wherein the aryl thereof is phenyl and the heterocyclenyl consists of about 5 to about 6 ring atoms. A fused arylheterocyclenyl as a variable may be bonded through any atom of the ring system thereof capable of such. The designation of the aza, oxa or thia as a prefix before heterocyclenyl portion of the fused arylheterocyclenyl define that at least a nitrogen, oxygen or sulfur atom is present respectively as a ring atom. The fused arylheterocyclenyl may be optionally substituted by one or more ring group substituent, wherein the "ring group substituent" is as defined herein. The nitrogen atom of a fused arylheterocyclenyl may be a basic nitrogen atom. The nitrogen or sulfur atom of the heterocyclenyl portion of the fused arylheterocyclenyl may also be optionally oxidized to the corresponding N-oxide, S-oxide or S,S-dioxide. Exemplary fused arylheterocyclenyl include 3H-indolinyl, 1H-2-oxoquinolyl, 2H-1-oxoisoquinolyl, 1,2-di-hydroquinolinyl, 3,4-dihydroquinolinyl, 1,2-dihydroisoquinolinyl, 3,4-dihydroisoquinolinyl, and the like.

"Fused arylheterocyclyl" means a fused aryl and heterocyclyl as defined herein. Preferred fused arylheterocyclyls are those wherein the aryl thereof is phenyl and the heterocyclyl consists of about 5 to about 6 ring atoms. A fused arylheterocyclyl as a variable may be bonded through any atom of the ring system thereof capable of such. The designation of the aza, oxa or thia as a prefix before heterocyclyl portion of the fused arylheterocyclyl define that at least a nitrogen, oxygen or sulfur atom is present respectively as a ring atom. The fused arylheterocyclyl may be optionally substituted by one or more ring group substituent, wherein the "ring group substituent" is as defined herein. The nitrogen atom of a fused arylheterocyclyl may be a basic nitrogen atom. The nitrogen or sulfur atom of the heterocyclyl portion of the fused arylheterocyclyl may also be optionally oxidized to the corresponding N-oxide, S-oxide or S,S-dioxide. Exemplary preferred fused arylheterocyclyl ring systems include indolinyl, 1,2,3,4-tetrahydroisoquinoline, 1,2,3,4-tetrahydroquinoline, 1H-2,3-dihydroisoindol-2-yl, 2,3-dihydrobenz[f]isoindol-2-yl, 1,2,3,4-tetrahydrobenz[g]-isoquinolin-2-yl, and the like.

"Fused heteroarylcycloalkenyl" means a fused heteroaryl and cycloalkenyl as defined herein. Preferred fused heteroarylcycloalkenyls are those wherein the heteroaryl thereof is phenyl and the cycloalkenyl consists of about 5 to about 6 ring atoms. A fused heteroaryl-cycloalkenyl as a variable may be bonded through any atom of the ring system thereof capable of such. The designation of the aza, oxa or thia as a prefix before heteroaryl portion of the fused heteroarylcycloalkenyl define that at least a nitrogen, oxygen or sulfur atom is present respectively as a ring atom. The fused heteroarylcycloalkenyl may be optionally substituted by one or more ring group substituent, wherein the "ring group substituent" is as defined herein. The nitrogen atom of a fused heteroarylcycloalkenyl may be a basic nitrogen atom. The nitrogen atom of the heteroaryl portion of the fused heteroarylcycloalkenyl may also be optionally oxidized to the corresponding N-oxide. Exemplary fused heteroarylcyclo-alkenyl include 5,6-dihydroquinolyl, 5,6-dihydroisoquinolyl, 5,6-dihydroquinoxalinyl, 5,6-dihydroquinazolinyl, 4,5-dihydro-1H-benzimidazolyl, 4,5-di-hydrobenzoxazolyl, and the like.

"Fused heteroarylcycloalkyl" means a fused heteroaryl and cycloalkyl as defined herein. Preferred fused heteroarylcycloalkyls are those wherein the heteroaryl thereof consists of about 5 to about 6 ring atoms and the cycloalkyl consists of about 5 to about 6 ring atoms. A fused heteroarylcycloalkyl as a variable may be bonded through any atom of the ring system thereof capable of such. The designation of the aza, oxa or thia as a prefix before heteroaryl portion of the fused heteroarylcycloalkyl define that at least a nitrogen, oxygen or sulfur atom is present respectively as a ring atom. The fused heteroarylcycloalkyl may be optionally substituted by one or more ring group substituent, wherein the "ring group substituent" is as defined herein. The nitrogen atom of a fused heteroarylcycloalkyl may be a basic nitrogen atom. The nitrogen atom of the heteroaryl portion of the fused heteroarylcycloalkyl may also be optionally oxidized to the corresponding N-oxide. Exemplary fused heteroarylcycloalkyl include 5,6,7,8-tetrahydroquinolinyl, 5,6,7,8-tetra-hydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like.

"Fused heteroarylheterocyclenyl" means a fused heteroaryl and heterocyclenyl as defined herein. Preferred fused heteroarylheterocyclenyls are those wherein the heteroaryl thereof consists of about 5 to about 6 ring atoms and the heterocyclenyl consists of about 5 to about 6 ring atoms. A fused heteroarylheterocyclenyl as a variable may be bonded through any atom of the ring system thereof capable of such. The designation of the aza, oxa or thia as a prefix before the heteroaryl or heterocyclenyl portion of the fused heteroarylhetero-cyclenyl define that at least a nitrogen, oxygen or sulfur atom is present respectively as a ring atom. The fused heteroarylheterocyclenyl may be optionally substituted by one or more ring group substituent, wherein the "ring group substituent" is as defined herein. The nitrogen atom of a fused heteroarylazaheterocyclenyl may be a basic nitrogen atom. The nitrogen or sulfur atom of the heteroaryl portion of the fused heteroarylheterocyclyl may also be optionally oxidized to the corresponding N-oxide. The nitrogen or sulfur atom of the heteroaryl or heterocyclyl portion of the fused heteroarylheterocyclyl may also be optionally oxidized to the corresponding N-oxide, S-oxide or S,S-dioxide. Exemplary fused heteroarylheterocyclenyl include 7,8-dihydro[1,7]naphthyridinyl, 1,2-dihydro[2,7]-naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl, 1,2-dihydro-2,6-naphthyridinyl, and the like.

"Fused heteroarylheterocyclyl" means a fused heteroaryl and heterocyclyl as defined herein. Preferred fused heteroarylheterocyclyls are those wherein the heteroaryl thereof consists of about 5 to about 6 ring atoms and the heterocyclyl consists of about 5 to about 6 ring atoms. A fused heteroarylheterocyclyl as a variable may be bonded through any atom of the ring system thereof capable of such. The designation of the aza, oxa or thia as a prefix before the heteroaryl or heterocyclyl portion of the fused heteroarylheterocyclyl define that at least a nitrogen, oxygen or sulfur atom is present respectively as a ring atom. The fused heteroarylheterocyclyl may be optionally substituted by one or more ring group substituent, wherein the "ring group substituent" is as defined herein. The nitrogen atom of a fused heteroarylheterocyclyl may be a basic nitrogen atom. The nitrogen or sulfur atom of the heteroaryl portion of the fused heteroarylheterocyclyl may also be optionally oxidized to the corresponding N-oxide. The nitrogen or sulfur atom of the heteroaryl or heterocyclyl portion of the fused heteroarylheterocyclyl may also be optionally oxidized to the corresponding N-oxide, S-oxide or S,S-dioxide. Exemplary fused heteroarylheterocyclyl include 2,3-dihydro-1H pyrrol[3,4-b]quinolin-2-yl, 1,2,3,4-tetrahydrobenz [b][1,7] naphthyridin-2-yl, 1,2,3,4-tetrahydrobenz [b][1,6]naphthyridin-2-yl, 1,2,3,4-tetra-hydro-9H-pyrido[3,4-b]indol-2yl, 1,2,3,4-tetrahydro-9H-pyrido[4,3-b]indol-2yl, 2,3-dihydro-1H-pyrrolo[3,4-b]indol-2-yl, 1H-2,3,4,5-tetrahydroazepino [3,4-b]indol-2-yl, 1H-2,3,4,5-tetra-hydroazepino[4,3-b]indol-3-yl, 1H-2,3,4,5-tetrahydroazepino[4,5-b]indol-2 yl, 5,6,7,8-tetra-hydro[1,7]napthyridyl, 1,2,3,4-tetrahydro[2,7]naphthyridyl, 2,3-dihydro[1,4]dioxino[2,3-b]pyridyl, 2,3-dihydro-[1,4]dioxino[2,3-b]pyridyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]-napthyridinyl, 1,2,3,4-tetrahydro[1,6]napthyridinyl, 1,2,3,4-tetrahydro[1,7]napthyridinyl, 1,2,3,4-tetrahydro[1,8]napthyridinyl, 1,2,3,4-tetra-hydro[2,6]napthyridinyl, and the like.

"Halo" means fluoro, chloro, bromo, or iodo. Preferred are fluoro, chloro or bromo, and more preferred are fluoro or chloro.

"Heteroaroyl" means an heteroaryl-CO— group wherein the heteroaryl group is as herein described. Exemplary groups include thiophenoyl, nicotinoyl, pyrrol-2-ylcarbonyl and 1- and 2-naphthoyl and pyridinoyl.

"Heteroaryl" means an aromatic monocyclic or multicyclic ring system of about 5 to about 14 carbon atoms, preferably about 5 to about 10 carbon atoms, in which one or more of the carbon atoms in the ring system is/are hetero element(s) other than carbon, for example nitrogen, oxygen or sulfur. Preferred ring sizes of rings of the ring system include about 5 to about 6 ring atoms. Encompassed by heteroaryl are fused heteroarylcycloalkenyl, fused heteroarylcycloalkyl, fused heteroarylheterocyclenyl and fused heteroarylheterocyclyl as defined herein when bonded through the heteroaryl moiety thereof. The "heteroaryl" may also be substituted by one or more "ring group substituents" which may be the same or different, and are as defined herein. The designation of the aza, oxa or thia as a prefix before heteroaryl define that at least a nitrogen, oxygen or sulfur atom is present respectively as a ring atom. A nitrogen atom of an heteroaryl may be a basic nitrogen atom and may also be optionally oxidized to the corresponding N-oxide. Exemplary heteroaryl and substituted heteroaryl groups include pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]

thiazolyl, benzofurazanyl, azaindolyl, benzimidazolyl, benzothienyl, thienopyridyl, thienopyrimidyl, pyrrolopyridyl, imidazopyridyl, benzoazaindolyl, 1,2,4-triazinyl, benzthiazolyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl. A preferred heteroaryl group is pyrazinyl.

"Heteroaryldiazo" means an heteroaryl-azo-group wherein the heteroaryl and azo groups are as defined herein.

"Heteroarylidyl" means a bivalent radical derived from a heteroaryl, wherein the heteroaryl is as described herein. A particular heteroaryldiyl radical is optionally substituted pyridinediyl.

"Heteroarylsulphonylcarbamoyl" means a heteroaryl-SO$_2$—NH—C(=O)— group wherein the heteroaryl group is as herein described.

"Heterocyclenyl" means a non-aromatic monocyclic or multicyclic hydrocarbon ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Preferred ring sizes of rings of the ring system include about 5 to about 6 ring atoms; and such preferred ring sizes are also referred to as "lower". Encompassed by heterocyclenyl are fused arylheterocyclenyl and fused heteroarylheterocyclenyl as defined herein when bonded through the heterocyclenyl moiety thereof. The designation of the aza, oxa or thia as a prefix before heterocyclenyl define that at least a nitrogen, oxygen or sulfur atom is present respectively as a ring atom. The heterocyclenyl may be optionally substituted by one or more ring group substituent, wherein the "ring group substituent" is as defined herein. The nitrogen atom of an heterocyclenyl may be a basic nitrogen atom. The nitrogen or sulfur atom of the heterocyclenyl may also be optionally oxidized to the corresponding N-oxide, S-oxide or S,S-dioxide. Exemplary monocyclic azaheterocyclenyl groups include 1,2,3,4-tetrahydrohydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Exemplary oxaheterocyclenyl groups include 3,4-dihydro-2H-pyran, dihydrofuranyl, and fluorodihydrofuranyl. An exemplary multicyclic oxahetero-cyclenyl group is 7-oxabicyclo[2.2.1]heptenyl. Exemplary monocyclic thiaheterocyclenyl rings include dihydrothiophenyl and dihydrothiopyranyl.

"Heterocyclyl" means a non-aromatic saturated monocyclic or multicyclic ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur. Preferred ring sizes of rings of the ring system include about 5 to about 6 ring atoms; and such preferred ring sizes are also referred to as "lower". Encompassed by heterocyclyl are fused arylheterocyclyl and fused heteroarylheterocyclyl as defined herein when bonded through the heterocyclyl moiety thereof. The designation of the aza, oxa or thia as a prefix before heterocyclyl define that at least a nitrogen, oxygen or sulfur atom is present respectively as a ring atom. The heterocyclyl may be optionally substituted by one or more "ring group substituents" which may be the same or different, and are as defined herein. The nitrogen atom of an heterocyclyl may be a basic nitrogen atom. The nitrogen or sulfur atom of the heterocyclyl may also be optionally oxidized to the corresponding N-oxide, S-oxide or S,S-dioxide. Exemplary monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Hydrate" means a solvate wherein the solvent molecule(s) is/are H$_2$O.

"N-oxysuccinimide" means a moiety of the following

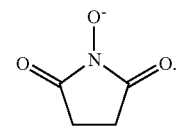

structure

"N-oxide" means a moiety of the following structure

"Patient" includes both human and other mammals.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulphamates and quinateslaurylsulphonate salts, and the like. See, for example S. M. Berge, et al., "pharmaceutical Salts," *J. Pharm. Sci.*, 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

Ring group substituents" mean substituents attached to aromatic or non-aromatic ring systems inclusive of aryl, heteroaryl, hydroxy, alkoxy, cyclyloxy, aryloxy, heteroaryloxy, acyl or its thioxo analogue, cyclylcarbonyl or its thioxo analogue, aroyl or its thioxo analogue, heteroaroyl or its thioxo analogue, acyloxy, cyclylcarbonyloxy, aroyloxy, heteroaroyloxy, halo, nitro, cyano, carboxy (acid), acid biostere, alkoxycarbonyl, cyclyloxycarbonyl, aryloxycarbonyl, heteroaryloxycarbonyl, alkylsulfonyl, cyclylsulfonyl, arylsulfonyl, heteroarylsulfonyl, alkylsulfinyl, cyclylsulfinyl, arylsulfinyl, heteroarylsulfinyl, alkylthio, cyclylthio, arylthio, heteroarylthio, cyclyl, aryldiazo, heteroaryldiazo, thiol, $Y^1Y^2N$—, $Y^1Y^2NC(O)$—, $Y^1Y^2NC(O)O$—, $Y^1Y^2NC(O)NY^3$— or $Y^1Y^2NSO_2$—, wherein $Y^1$, $Y^2$ and $Y^3$ are independently hydrogen, optionally substituted alkyl, optionally substituted aryl or optionally substituted heteroaryl, or for where the substituent is $Y^1Y^2N$—, then one of $Y^1$ and $Y^2$ may be acyl, cyclylcarbonyl, aroyl, heteroaroyl, alkoxycarbonyl, cyclyloxycarbonyl, aryloxycarbonyl or heteroaryloxycarbonyl, as defined herein and the other of $Y^1$ and $Y^2$ is as defined previously, or for where the substituent is $Y^1Y^2NC(O)$—, $Y^1Y^2NC(O)O$—, $Y^1Y^2NC(O)NY^3$— or $Y^1Y^2NSO_2$—, $Y^1$ and $Y^2$ may also be taken together with the N atom through which $Y^1$ and $Y^2$ are linked to form a 4 to 7 membered azaheterocyclyl or azaheterocyclenyl. When a ring system is saturated or partially saturated, the "ring group substituents" further include, methylene ($H_2C$=), oxo (O=) and thioxo (S=). Acidic/amide ring group substituents are carboxy (acid), acid biostere and $Y^1Y^2NCO$—. Non-acidic polar ring group substituents are hydroxy, oxo (O=), thioxo (S=), acyl or its thioxo analogue, cyclylcarbonyl or its thioxo analogue, aroyl or its thioxo analogue, heteroaroyl or its thioxo analogue, alkoxycarbonyl, cyclyloxycarbonyl, aryloxycarbonyl, heteroaryloxycarbonyl, acyloxy, cyclylcarbonyloxy, aroyloxy, heteroaroyloxy, alkylsulfonyl, cyclylsulfonyl, arylsulfonyl, heteroarylsulfonyl, alkylsulfinyl, cyclylsulfinyl, arylsulfinyl, heteroarylsulfinyl, thiol, $Y^1Y^2N$—, $Y^1Y^2NC(O)$—, $Y^1Y^2NC(O)O$—, $Y^1Y^2NC(O)NY^3$— or $Y^1Y^2NSO_2$—.

"Solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

The term "aqueous methanol" refers to a mixture of methanol and water, preferably methanol comprising about 40% to about 60% water; more preferably about 1:1 methanol and water.

EMBODIMENTS

In a first embodiment of the present invention, a method is provided for preparing a monoacylated glycopeptide acylated at the N1 or N2 position thereof. The method includes acylating a parent glycopeptide, selected from the group consisting of A82846A, A82846B, A82846C and PA-42867-A, with an activated ester selected from N-acyl-hydroxysuccinimide and N-acyl-hydroxyphthalimide in dimethylsulfoxide to yield the monoacylated glycopeptide.

In a preferred embodiment, the activated ester is an N-acyl-hydroxysuccinimide of formula Ia

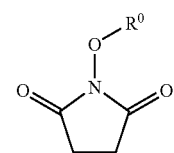

Ia wherein:

$R^0$ is $C_2$-$C_{13}$ alkanoyl, or a group of formula Ia'

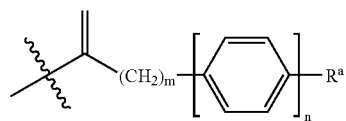

Ia' m is an integer from 0 to 15;

n is 0, 1 or 2, provided that m+n does not equal 0; and $R^a$ is H, halo, $C_1$-$C_8$ alkyl, $C_1$-$C_8$ alkoxy, —$NH_2$, —NH ($C_1$-$C_3$ alkyl) or —$N((C_1$-$C_3)alkyl)_2$.

In another preferred embodiment, the monoacylated glycopeptide is of formula I

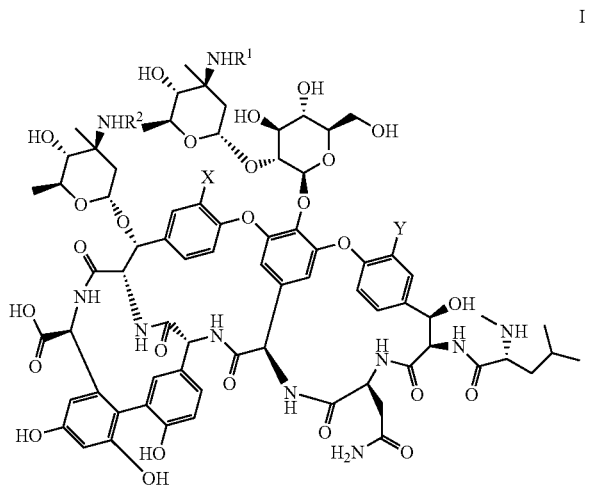

I wherein:

X and Y are independently hydrogen or chloro;

$R^1$ is $C_2$-$C_{13}$ alkanoyl, or a group of formula Ia'

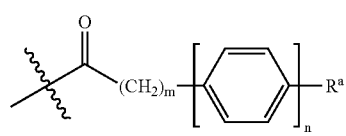

Ia'

$R^2$ is H;

m is an integer from 0 to 15;

n is 0, 1 or 2, provided that m+n does not equal 0; and $R^a$ is H, halo, $C_1$-$C_8$ alkyl, $C_1$-$C_8$ alkoxy, —$NH_2$, —NH($C_1$-$C_3$ alkyl) or —N(($C_1$-$C_3$)alkyl)$_2$.

In yet another preferred embodiment, the monoacylated glycopeptide is of formula II

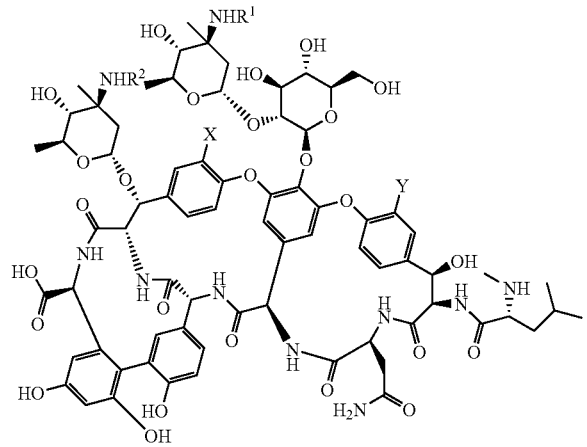

II wherein:

X and Y are independently hydrogen or chloro;

$R^1$ is hydrogen;

$R^2$ is $C_2$-$C_{13}$ alkanoyl, or a group of formula Ia'

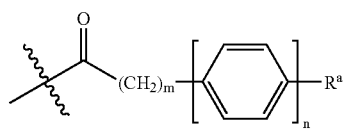

Ia' m is an integer from 0 to 15, n is 0, 1 or 2, provided that m+n does not equal 0; and $R^a$ is H, halo, $C_1$-$C_8$ alkyl, $C_1$-$C_8$ alkoxy, —$NH_2$, —NH($C_1$-$C_3$ alkyl) or —N(($C_1$-$C_3$)alkyl)$_2$.

In a second embodiment of the present invention, a method is provided for preparing a monoacylated glycopeptide acylated at the N3 position thereof. The method includes acylating a parent glycopeptide, which is selected from the group consisting of A82846A, A82846B, A82846C and PA-42867-A, with an activated ester selected from N-acyl-hydroxysuccinimide and N-acyl-hydroxyphthalimide in aqueous methanol to yield the monoacylated glycopeptide.

In a preferred embodiment, the aqueous methanol includes about 40% to about 60% water.

In a more preferred embodiment, the aqueous methanol includes is about a 1:1 mixture of methanol and water).

In another preferred embodiment, the activated ester is an N-acyl-hydroxysuccinimide of formula Ia

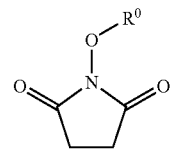

Ia wherein:

$R^0$ is $C_2$-$C_{13}$ alkanoyl, or a group of formula Ia'

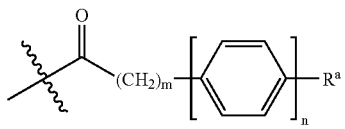

Ia' m is an integer from 0 to 15;

n is 0, 1 or 2, provided that m+n does not equal 0; and $R^a$ is H, halo, $C_1$-$C_8$ alkyl, $C_1$-$C_8$ alkoxy, —$NH_2$, —NH($C_1$-$C_3$ alkyl) or —N(($C_1$-$C_3$)alkyl)$_2$.

In yet another preferred embodiment, the monoacylated glycopeptide is of formula III

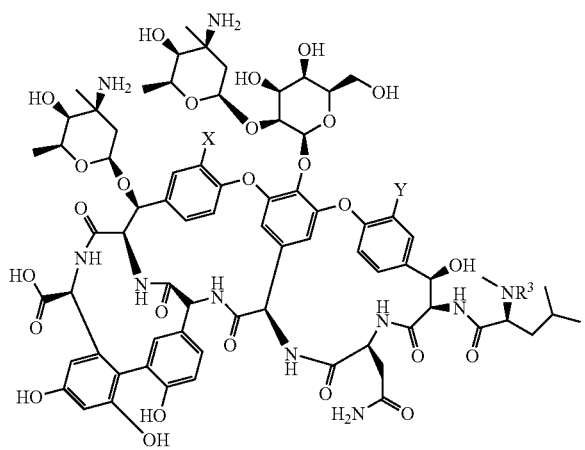

III wherein:

X and Y are independently hydrogen or chloro;

$R^3$ is $C_2$-$C_{13}$ alkanoyl, or a group of formula Ia'

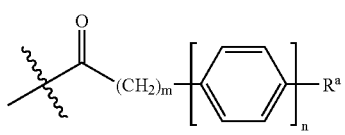

Ia' m is an integer from 0 to 15;

n is 0, 1 or 2, provided that m+n does not equal 0; and $R^a$ is H, halo, $C_1$-$C_8$ alkyl, $C_1$-$C_8$ alkoxy, —$NH_2$, —NH($C_1$-$C_3$ alkyl) or —N(($C_1$-$C_3$)alkyl)$_2$.

In a third embodiment of the invention, an N-monoacylated glycopeptide is provided of formula IV

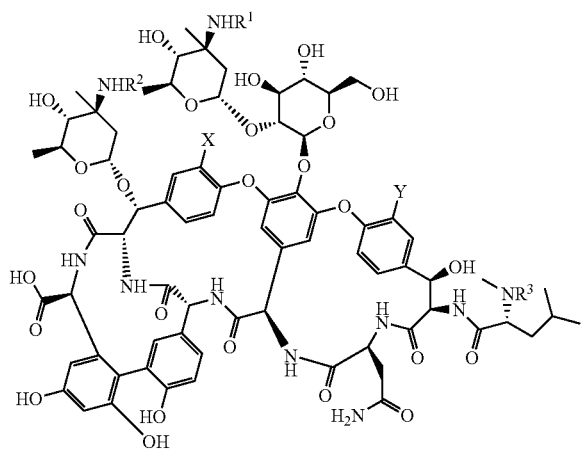

and pharmaceutically acceptable salts thereof;

wherein:

X and Y are independently hydrogen or chloro;

$R^1$, $R^2$, and $R^3$ are independently H, $C_2$-$C_{13}$ alkanoyl, or a group of formula Ia'

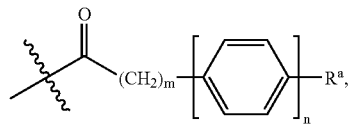

and two of R1, R2 and R3 are hydrogen;

m is an integer from 0 to 15;

n is 0, 1 or 2, provided that m+n does not equal 0; and $R^a$ is H, halo, $C_1$-$C_8$ alkyl, $C_1$-$C_8$ alkoxy, —$NH_2$, —NH ($C_1$-$C_3$ alkyl) or —N(($C_1$-$C_3$)alkyl)$_2$.

In a preferred embodiment, the monoacylated glycopeptide is of formula I

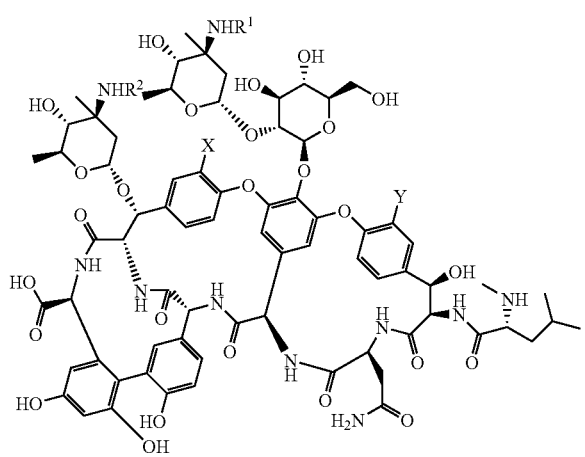

and pharmaceutically acceptable salts thereof;

wherein:

X and Y are independently hydrogen or chloro;

$R^1$ is $C_2$-$C_{13}$ alkanoyl, or a group of formula Ia'

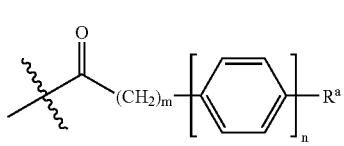

$R^2$ is H;

m is an integer from 0 to 15;

n is 0, 1 or 2, provided that m+n does not equal 0; and $R^a$ is H, halo, $C_1$-$C_8$ alkyl, $C_1$-$C_8$ alkoxy, —$NH_2$, —NH ($C_1$-$C_3$ alkyl) or —N(($C_1$-$C_3$)alkyl)$_2$.

In another preferred embodiment, the monoacylated glycopeptide is of formula II

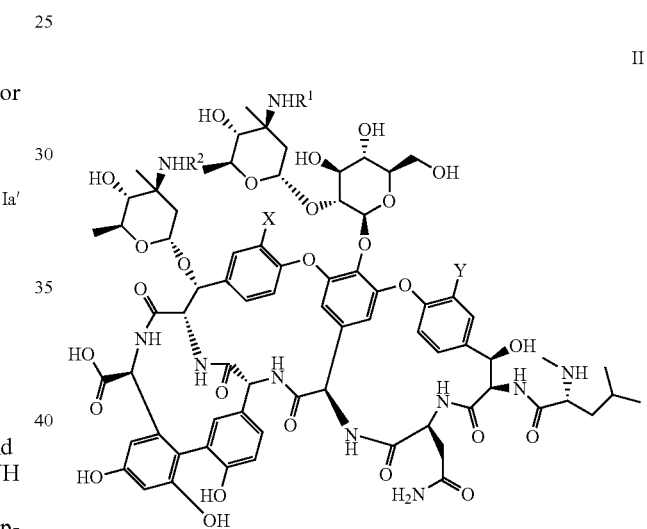

and pharmaceutically acceptable salts thereof;

wherein:

X and Y are independently hydrogen or chloro;

$R^1$ is hydrogen; $R^2$ is $C_2$-$C_{13}$ alkanoyl, or a group of formula Ia'

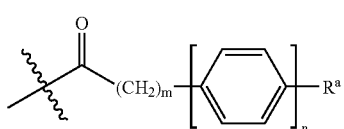

m is an integer from 0 to 15;

n is 0, 1 or 2, provided that m+n does not equal 0; and $R^a$ is H, halo, $C_1$-$C_8$ alkyl, $C_1$-$C_8$ alkoxy, —$NH_2$, —NH ($C_1$-$C_3$ alkyl) or —N(($C_1$-$C_3$)alkyl)$_2$.

In yet another preferred embodiment, the monoacylated glycopeptide is of formula III

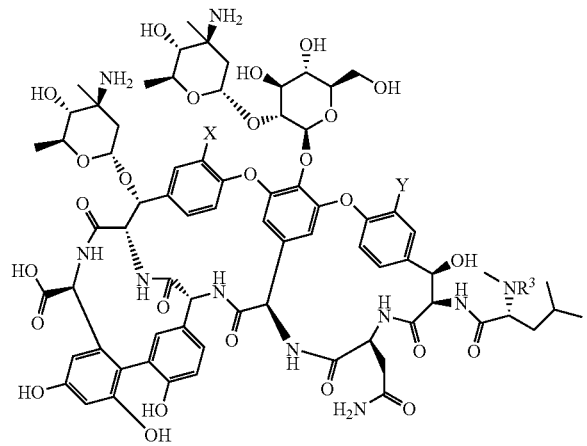

III and pharmaceutically acceptable salts thereof;
wherein:
X and Y are independently hydrogen or chloro;
$R^3$ is $C_2-C_{13}$ alkanoyl, or a group of formula Ia'

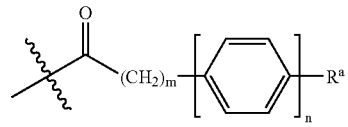

Ia' m is an integer from 0 to 15;
n is 0, 1 or 2, provided that m+n does not equal 0; and
$R^a$ is H, halo, $C_1-C_8$ alkyl, $C_1-C_8$ alkoxy, —$NH_2$, —NH($C_1-C_3$ alkyl) or —N(($C_1-C_3$)alkyl)$_2$.

In a more preferred embodiment, any one of $R^0$, $R^1$, $R^2$, or $R^3$ is selected from 4-phenylbenzoyl, 4-(4'-chlorophenyl)benzoyl, 4-octyloxybenzoyl, octanoyl, and 8-phenyloctanoyl.

In a fourth embodiment of the invention, a pharmaceutical composition is provided, which includes a pharmaceutically-acceptable amount of an N-monoacylated glycopeptide of any one of formulas I to IV together with a pharmaceutically-acceptable carrier.

A fifth embodiment of the invention provides the use of an N-monoacylated glycopeptide of any one of formulas I to IV, or a pharmaceutically acceptable salt thereof, for treating an infection caused by *staphylococci*.

In a preferred embodiment, the *staphylococci* is a coagulase-negative strain.

A sixth embodiment of the invention provides the use of an N-monoacylated glycopeptide of any one of formulas I to IV, or a pharmaceutically acceptable salt thereof, for the manufacture of a medicament for the treatment of an infection caused by *staphylococci*.

In a preferred embodiment, the *staphylococci* is a coagulase-negative strain.

A seventh embodiment provides a method of controlling the growth of a microorganism susceptible to the antimicrobial activity of an N-monoacylated glycopeptide antibiotic of any one of formulas I to IV, comprising providing a growth-controlling effective amount of said glycopeptide antibiotic to a locus where said microorganism is present.

An eighth embodiment provides a method of controlling the growth of a microorganism susceptible to the antimicrobial activity of an N-monoacylated glycopeptide antibiotic of any one of formulas I to IV, comprising contacting said microorganism and a growth-controlling effective amount of said glycopeptide antibiotic.

This invention also includes all combinations of particular and preferred embodiments described herein.

Preparation of Compounds of the Invention

After numerous attempts with a variety of amino acid acylation conditions, Applicants surprisingly discovered that one can selectively acylate the N1 or N2 positions of an A82846 glycopeptide such as A82846A, A82846B, A82846C or PA-42867-A by acylating the parent glycopeptide with an activated ester such as N-acyl-hydroxysuccinimide or N-acyl-hydroxyphthalimide in DMSO. Alternatively, the N3 position is selectively acylated when the parent glycopeptide is acylated with an activated ester such as N-acyl-hydroxysuccinimide or N-acyl-hydroxyphthalimide in aqueous methanol.

For a general discussion on such activated esters, see M. Bodanszky in "Principles of Peptide Synthesis," pp. 32-35, Springer-Verlag, 1984. Applicants have discovered that N-acyl-hydroxysuccinimide or N-acyl-hydroxyphthalimide provide for selective acylation in a designated solvent, such as DMSO or an aqueous methanol mixture. N-acyl-hydroxysuccinimide and N-acyl-hydroxyphthalimide activated esters are prepared using standard acid/alcohol condensation chemistry well know to those skilled in the art. (see, e.g., M. Bodanszky and A. Bodanszky in "The Practice of Peptide Synthesis," Springer-Verlag, pp. 124-125, 1984)

The A82846 glycopeptide analogs (A82846A, A82846B, A82846C and PA-42867-A) may be prepared using standard procedures well known in the art. (see, e.g., U.S. Pat. No. 4,946,941; EP 265,071 and EP 231,111).

The reaction of the N-acyl-hydroxysuccinimide or N-acyl-hydroxyphthalimide with the glycopeptide is generally carried out at a temperature between about 50° C. and about 110° C. (preferably between about 60° C. and 80° C.) for about 15 to 24 hours (preferably 16 to 20 hours) in the appropriate designated solvent. The temperature and reaction time may vary depending upon the solubility of the starting materials. When DMSO is used as the solvent, Dimethylformamide (DMF) may also be present as a co-solvent in amounts up to about 40%. However, DMF alone did not provide significant amounts of the desired acylated products. The ratio of the activated ester to glycopeptide is generally from about 2:1 to about 3:1.

The acylated products may be isolated using methodology known in the art, for example, using reverse-phase HPLC conditions employing a pH 3 phosphate buffer and acetonitrile. The isolated products may be used per se or in the form of its pharmaceutically acceptable salt or solvate. The following set of examples illustrate the general reaction conditions for selectively acylating either the N1 or N2 positions, or the N3 position of a A82846A, A82846B, A82846C, or PA-42967-A glycopeptide.

EXAMPLES

Unless indicated otherwise, all chemicals can be acquired from commercial suppliers such as Aldrich Chemical (Milwaukee, Wis.), Sigma, and other commercial sources well-known to those skilled in the art.

Analytical Testing Methods

Fast atom bombardment mass spectroscopy (FAB-MS) is utilized to determine the site of acylation for the purified products. See e.g., Nagarajan, R., et al., *J. Antibiotics*, 41, 1430-1438 (1988); and Roberts, G. D., et al., *J. Antibiotics*, 38, 713-720 (1985). Observation of the molecular ion indicates that the desired acyl derivative is obtained and then the fragmentation pattern is used to determine the site of acylation according to the following Table I:

TABLE I

| Site of Acylation | N1 | N2 | N3 |
|---|---|---|---|
| Molecular ion: | 1591.5 + R − H | 1591.5 + R − H | 1591.5 + R − H |
| Fragments: | 1591.5 − S1 − S2 | 1591.5 + R − S1 | 1591.5 + R − S1 − S3 |
|  | | 1591.5 − S3 | 1591.5 + R − S1 − S2 − S3 |

While other fragments are observed for each regioisomeric acyl derivative, these represent the unique fragment(s) observed for each.

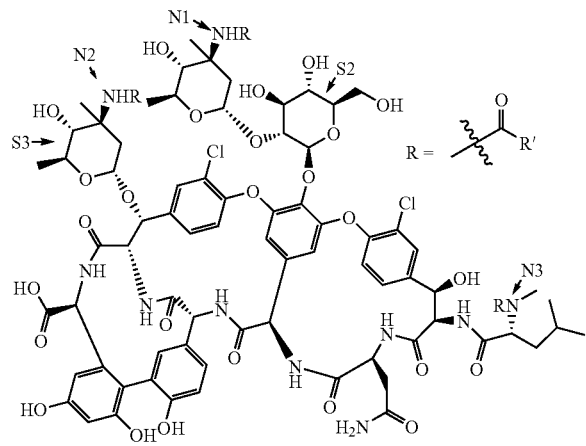

S1, S2 and S3 represent the sugar moiety indicated by the arrows in the structure above. N1, N2 and N3 identify the acylation site.

HPLC Methods

Analytical: Reactions are monitored by analytical HPLC using a Waters μbondapak $C_{18}$ column (3.9×300 mm) and UV detection at 280 nm. Elution is accomplished with a linear gradient of 5% $CH_3CN$: 95% buffer to 80% $CH_3CN$: 20% buffer over 30 minutes. The buffer is 0.5% triethylamine in water, adjusted to pH 3 with $H_3PO_4$.

Preparative (Condition A): Crude reaction mixtures are purified by preparative HPLC using a Waters Nova-Pak column (40×300 mm) and UV detection at 280 nm. Elution is accomplished with a linear gradient of 5% $CH_3CN$: 95% buffer to 80% $CH_3CN$: 20% buffer over 30 minutes. The buffer is 0.5% triethylamine in water, that is adjusted to pH 3 with $H_3PO_4$. The desired fractions are subsequently desalted with a Waters $C_{18}$ Sep-Pak (10 cc) followed by lyophilization.

Semi-Preparative (Condition B): Impure products are purified by semi-preparative HPLC using a Zorbax $C_{18}$ column (21.2 mm×25 cm) and UV detection at 280 nm. Elution is accomplished with a linear gradient of 5% $CH_3CN$: 95% buffer to 80% $CH_3CN$: 20% buffer over 30 minutes. The buffer is 0.5% triethylamine in water, that is adjusted to pH 3 with $H_3PO_4$. The desired fractions are subsequently desalted with a Waters $C_{18}$ Sep-Pak (10 cc) followed by lyophilization.

Examples 1 and 2

Examples 1 and 2 illustrate the process for selectively acylating the N1 and N2 positions, respectively.

Preparation of 4'-N-octanoyl-A82846B (Compound I, where $R^1$=n-octanoyl; X and Y=Cl) and 6'-N-octanoyl-A82846B (Compound II, where $R^2$=n-octanoyl; X and Y=Cl)

A82846B (390 mg, 0.245 mmol) is dissolved in DMSO (40 ml) and treated with succinyl octanoate (127 mg, 0.527 mmol). The resulting mixture is heated to 75° C. for 17 hours. Then, the reaction is cooled to room temperature, diluted with water (500 ml), and lyophilized to yield a solid. The crude material is redissolved in 1:1 $CH_3CN:H_2O$ (15 ml) and purified by preparative HPLC (condition A) The desired fractions, as determined by analytical HPLC, are concentrated in vacuo to 3 ml and desalted. After lyophilization, 4'-N-octanoyl-A82846B is obtained (7 mg, 0.0041 mmol, 1.7%) as a white powder. FAB-MS: 1719.7

6'-N-octanoyl-A82846B is obtained as an impure solid and repurified by semi-preparative HPLC (condition B). The desired fractions, as determined by analytical HPLC, are concentrated in vacuo to 3 ml, and desalted. After lyophilization, 6'-N-octanoyl-A82846B is obtained (3 mg, 0.0017 mmol, 0.7%) as a white powder. FAB-MS: 1718.5

Example 3

Example 3 illustrates the process for selectively acylating the N3 position.

Preparation of 1'-N-octanoyl-A82846B (Compound III where R3=n-octanoyl; X and Y=Cl)

A82846B (235 mg, 0.148 mmol) is dissolved in 1:1$H_2O$: MeOH (22 ml) and treated with succinyl octanoate (93 mg, 0.386 mmol). The resulting mixture is heated to 75° C. for 19 hours. Then, the reaction is cooled to room temperature and concentrated in vacuo to give a solid. The crude material is redissolved in 1:1 $CH_3CN:H_2O$ (15 ml) and purified by preparative HPLC (condition A). The desired fractions, as determined by analytical HPLC, are concentrated in vacuo to 3 ml and desalted. After lyophilization, 1'-N-octanoyl-A82846B is obtained (30 mg, 0.0175 mmol, 11.8%) as a white powder. FAB-MS: 1719.4

The corresponding N1, N2 and N3 substituted 4-phenyl-benzoyl, 4-(4'-chlorophenyl)-benzoyl, 4-n-octanoxy-benzoyl, and 8-phenyl-n-octanoyl derivatives are also prepared using the same general procedures described in Examples 1 to 3. (see Table II below)

TABLE II

| Example No. | Site of Acylation | Sidechain | Yield | FAB-MS |
|---|---|---|---|---|
| 1 | N1 | 4-phenylbenzoyl | 2.4% | 1773.2 |
| 2 | N2 | 4-phenylbenzoyl | 8.7% | 1773.5 |
| 3 | N3 | 4-phenylbenzoyl | | 1772.7 |
| 4 | N1 | 4-(4'-chlorophenyl)benzoyl | 0.6% | 1807.3 |
| 5 | N2 | 4-(4'-chlorophenyl)benzoyl | 2.2% | 1807.7 |
| 6 | N1 | 4-octyloxybenzoyl | 0.5% | 1825.0 |
| 7 | N2 | 4-octyloxybenzoyl | 2.1% | 1825.6 |
| 8 | N1 | octanoyl | 1.7% | 1719.7 |
| 9 | N2 | octanoyl | 0.7% | 1718.5 |
| 10 | N3 | octanoyl | 11.8% | 1719.4 |
| 11 | N1 | 8-phenyloctanoyl | 1.8% | 1794.4 |
| 12 | N2 | 8-phenyloctanoyl | 4.6% | 1795.5 |
| 13 | N3 | 8-phenyloctanoyl | 7.3% | 1795.5 |

Pharmacology

The compounds of the present invention have in vitro activity against Gram-positive pathogenic bacteria. The antibacterial activity of the present compounds is illustrated in Tables III and IV. The minimal inhibitory concentrations (MICs) were determined using a standard broth microdilution assay. Table IV presents a comparison of the activity of illustrative compounds against representative vancomycin-resistant and vancomycin-sensitive enterococci (*Enterococcus faecium* and *Enterococcus faecalis*), mean geometric MIC (mcg/mL), as determined by the standard broth microdilution assay.

Assays for antimicrobial activity were performed using microbroth susceptibility testing methods as described by the NCCLS (National Committee for Clinical Laboratories Standards. 1990. Approved standard M7-A2. Methods for dilution antimicrobial susceptibility testing for bacteria that grow aerobically, 2 ed., Villanova Pa.). Brain-heart infusion medium (BHI) was used for testing of *enterococci*, and NCCLS recommendations for medium were followed for other bacteria.

As indicated above, the compounds of the present invention have activity against both *staphylococci* (including methicillin-resistant and vancomycin-intermediate *staphylococcus aureus* strains) and *enterococci* (including vancomycin-resistant *enterococci* and vancomycin-susceptible isolates). For a discussion of vancomycin-intermediate *Staphylococcus aureus* (VISA) strains see, e.g., F. C. Tenover, M. V. Lancaster, N. C. Hill, C. D. Steward, S. A. Stocker, G. A. Hancock, C. M. O'hara, N. C. Clark, and K. Hiramatsu, "Characterization of *staphylococci* with reduced susceptibilities to vancomycin and other glycopeptides," *J. Clinical Microbiol.* 36(4), 1020-1027 (1998). The compounds are particularly active against *staphylococci*, especially coagulase-negative *staphylococci* (i.e., non-*aureus* strains). Thus, the compounds of the present invention provide useful alternative treatments especially for those infections resistant to known therapies.

TABLE III

In Vitro Antimicrobial Activity
MIC (μg/ml)/Compound

| Organism | Example No. | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Staphylococcus aureus 446 | 2 | 8 | 0.5 | 1 | 0.5 | 2 | ≦.06 | 2 | 1 | 1 | 1 | 0.125 | 0.5 |
| Staphylococcus aureus 489 | 0.5 | 0.5 | 0.5 | 0.25 | ≦.06 | 1 | ≦.06 | 0.25 | 0.125 | 0.25 | 0.25 | ≦.06 | 0.125 |
| Staphylococcus aureus 447 | 16 | 32 | 16 | 4 | 2 | 8 | 0.125 | 8 | 2 | 1 | 2 | 2 | 0.5 |
| Staphylococcus aureus X400 | 1 | 2 | 0.5 | 0.25 | ≦.06 | 4 | 0.125 | 0.5 | 0.5 | 0.5 | 0.5 | 0.125 | 0.25 |
| Staphylococcus aureus X778 | 1 | 2 | 1 | 0.25 | 0.5 | 2 | 0.125 | 1 | 0.25 | 0.5 | 0.125 | ≦.06 | 0.25 |
| Staphylococcus aureus 491 | 0.25 | 1 | 0.5 | 0.5 | ≦.06 | 2 | ≦.06 | 0.25 | 0.125 | 0.25 | 0.125 | ≦.06 | 0.125 |
| Staphylococcus aureus S13E | 2 | 4 | 0.25 | 0.5 | 0.5 | 8 | ≦.06 | 2 | 1 | 0.5 | 0.25 | ≦.06 | 0.5 |
| Staphylococcus aureus SA1199 | 2 | 4 | 1 | 0.5 | 0.5 | 4 | ≦.06 | 2 | 0.5 | 0.5 | 1 | 0.25 | 0.5 |
| Staphylococcus aureus SA1199A | 0.125 | 1 | 1 | 0.25 | ≦.06 | 0.25 | ≦.06 | 0.25 | 0.125 | 0.125 | ≦.06 | ≦.06 | ≦.06 |
| Staphylococcus aureus SA1199B | 2 | 2 | 2 | 0.5 | 0.25 | 2 | ≦.06 | 2 | 0.5 | 0.5 | 0.25 | 0.125 | 0.25 |
| Staphylococcus haemolyticus 105 | 1 | 2 | 4 | 1 | 0.5 | 0.5 | ≦.06 | 0.5 | 0.25 | 1 | ≦.06 | ≦.06 | ≦.06 |
| Staphylococcus haemolyticus 415 | 8 | >64 | 2 | 4 | 8 | 8 | 8 | 16 | 16 | 16 | 4 | 8 | 8 |
| Staphylococcus epidermidis 270 | 16 | 32 | 2 | 2 | 4 | 8 | ≦.06 | 8 | 2 | 0.5 | 1 | 2 | 0.25 |
| Enterococcus faecium 180 | 0.25 | 32 | 0.25 | ≦.06 | 1 | 0.25 | 0.5 | 2 | 32 | 32 | 0.5 | 2 | 8 |
| Enterococcus faecium 180-1 | ≦.06 | 1 | ≦.06 | ≦.06 | ≦.06 | 0.125 | ≦.06 | 0.125 | 0.125 | ≦.06 | ≦.06 | ≦.06 | ≦.06 |
| Enterococcus faecalis 2041 | 0.125 | 1 | ≦.06 | ≦.06 | ≦.06 | 0.25 | ≦.06 | 0.25 | 0.5 | 0.25 | ≦.06 | ≦.06 | 0.25 |

TABLE III-continued

In Vitro Antimicrobial Activity
MIC (µg/ml)/Compound

| Organism | Example No. | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Enterococcus faecalis 276 | 0.5 | 1 | 0.125 | 0.125 | ≦.06 | 1 | ≦.06 | 0.5 | 0.125 | 0.25 | 0.25 | ≦.06 | 0.25 |
| Enterococcus gallinarum 245 | 8 | >64 | 2 | 4 | 8 | 8 | 8 | 16 | 16 | 2 | 4 | 8 | 2 |
| Haemophilus influenzae RD | >64 | >64 | >64 | 0.25 | >64 | >64 | >64 | 64 | 64 | | | | |
| Escherichia coli EC14 | >64 | >64 | >64 | >64 | >64 | >64 | >64 | >64 | >64 | >64 | >64 | >64 | >64 |
| Streptococcus pyogenes C203 | ≦.06 | ≦.06 | ≦.06 | 0.125 | ≦.06 | 0.125 | ≦.06 | ≦.06 | ≦.06 | ≦.06 | ≦.06 | ≦.06 | ≦.06 |
| Streptococcus pneumoniae P1 | ≦.06 | ≦.06 | ≦.06 | 0.125 | ≦.06 | 0.25 | ≦.06 | ≦.06 | ≦.06 | ≦.06 | ≦.06 | ≦.06 | ≦.06 |

TABLE IV

In Vitro Activity Against Enterococci
Mean geometric MIC (µg/ml)

| Example No. | Vancomycin Resistant Strains | Vancomycin Sensitive Strains |
|---|---|---|
| 1 | 11.3 | 0.38 |
| 2 | >25 | 0.38 |
| 3 | 4 | 0.19 |
| 4 | 3.4 | 0.093 |
| 5 | 19 | 0.29 |
| 6 | 11.3 | 1.2 |
| 7 | 6.7 | 0.06 |
| 8 | 54 | 0.87 |
| 9 | >90 | 1.2 |
| 10 | 90 | 2.3 |
| 11 | 9.5 | 0.093 |
| 12 | 45 | 0.33 |
| 13 | >51 | 1.5 |

Consequently, the acylated glycopeptide compounds prepared by the processes described herein are useful in treating infections caused by methicillin-resistant *staphylococci*, as well as vancomycin-resistant and vancomycin-susceptible *enterococci*. The compounds are particularly useful for treating infections caused by *staphylococci*, more particularly coagulase-negative strains of *staphylococci*. Accordingly, the acylated glycopeptide compounds (including the formulations) are useful in the manufacture of a medicament for the therapeutic applications described herein.

The compositions disclosed herein can also be used to control the growth of microorganisms susceptible to the antimicrobial activity of the N-monoacylated glycopeptide antibiotics discussed herein. By "control the growth" is meant retarding or inhibiting the growth of, stopping the growth of, or killing, the microorganism. This results in a reduction in the adverse effects caused by the presence of the microorganism in any particular locus or milieu. These compositions can be formulated by conventional methods, and can contain formulation aids such as carriers, diluents, inert materials, surfactants, solvents, and other additives well known in the art. Pharmaceutically acceptable carriers are disclosed, for example, in The Pharmacopeia of the United States and the National Formulary. Using these formulations, the present N-monoacylated glycopeptide antibiotics, alone or in combination with other antimicrobial substances, such as antibiotics, antifungals, etc., can also be prepared. Numerous conventional antibiotics and antifungals with which the present peptides and metal ions can be used are known in the art.

The methods of the present invention for controlling the growth of microorganisms can be carried out in a variety of ways. The N-monoacylated glycopeptide antibiotics and compositions discussed herein can be applied directly to loci where undesirable microorganisms are present, alone or in a mixture with other active ingredients, carriers, diluents, or other additives, including other antimicrobial agents, as is known in the art. The locus can be an inert surface, a surface of a mammal, or a surface of a plant. Inert surfaces include, for example, surfaces of medical and surgical equipment, laboratory bench tops, hospital room and hospital operating room equipment, walls, floors, and sinks.

Furthermore, another invention herein is directed to a method of treating a patient suffering from or subject to a staphylococcal infection comprising administering to the patient a pharmaceutically effective amount of compound of any one of formulas I to IV. References herein to treating a staphylococcal infection should be understood to include prophylactic therapy to prevent or inhibit the infection as well as the treatment of an established acute or chronic staphylococcal infection or physiological conditions associated with staphylococcal infection to essentially cure the patient of the infection, inhibit the degree (amount) of infection or ameliorate the physiological conditions associated therewith. "Effective amount" is meant to describe an amount of the compound of the present invention effective within the scope of reasonable biological judgement, suitable for use in contact with the cells of humans and other mammals without undue toxicity, irritation, allergic response and the like, and are commensurate with a reasonable benefit/risk ratio in treating a staphylococcal infection and thus producing the desired therapeutic effect.

Physiological conditions discussed herein include some, but not all, of the possible clinical situations where a anti-staphylococcal treatment is warranted. Those experienced in this field are well aware of the circumstances requiring either an anti-staphylococcal treatment.

A particular aspect of the invention provides for a compound according to the invention to be administered in the form of a pharmaceutical composition, though the compound may be administered alone. "Pharmaceutical composition" means to a composition comprising a compound of any one of formulas I to IV and at least one component selected from the group comprising pharmaceutically acceptable carriers, diluents, coatings, adjuvants, excipients, or vehicles, such as preserving agents, fillers, disintegrating agents, wetting agents, emulsifying agents, emulsion stabilizing agents, suspending agents, isotonic agents, sweetening agents, flavoring agents, perfuming agents, coloring agents, antibacterial agents, antifungal agents, other therapeutic agents, lubricating agents, adsorption delaying or promoting agents, and dispensing agents, depending on the nature of the mode of administration and dosage forms. The compositions may be presented in the form of tablets, pills, granules, powders, aqueous solutions or suspensions, injectable solutions, elixirs or syrups. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Examples of antibacterial and antifungal agents for the prevention of the action of microorganisms include parabens, chlorobutanol, phenol, sorbic acid, and the like. Examples of isotonic agents include sugars, sodium chloride and the like. Examples of adsorption delaying agents to prolong absorption include aluminum monosterate and gelatin. Examples of adsorption promoting agents to enhance absorption include dimethyl sulphoxide and related analogs. Examples of suitable carriers, diluents, solvents, vehicles, solubilizing agents, emulsifiers and emulsion stabilizers, include water, chloroform, sucrose, ethanol, isopropyl alcohol, ethyl carbonate, ethyl acetate, benzyl alcohol, tetrahydrofurfuryl alcohol, benzyl benzoate, polyols, propylene glycol, 1,3-butylene glycol, glycerol, polyethylene glycols, dimethyl-formamide, Tween® 60, Span® 80, cetostearyl alcohol, myristyl alcohol, glyceryl mono-stearate and sodium lauryl sulfate, fatty acid esters of sorbitan, vegetable oils (such as cottonseed oil, groundnut oil, corn germ oil, olive oil, castor oil and sesame oil) and injectable organic esters such as ethyl oleate, and the like, or suitable mixtures of these substances. Examples of excipients include lactose, milk sugar, sodium citrate, calcium carbonate, dicalcium phosphate. Examples of disintegrating agents include starch, alginic acids and certain complex silicates. Examples of lubricants include magnesium stearate, sodium lauryl sulphate, talc, as well as high molecular weight polyethylene glycols.

Other therapeutic agents may be used in combination with a compound of the present invention, including any other antibiotics.

The choice of material in the pharmaceutical composition other than the compound of any of formulas I to IV is generally determined in accordance with the chemical properties of the active compound such as solubility, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets.

The pharmaceutical compositions may be presented in assorted forms such as tablets, pills, granules, powders, aqueous solutions or suspensions, injectable solutions, elixirs or syrups.

"Liquid dosage form" means the dose of the active compound to be administered to the patient is in liquid form, for example, pharmaceutically acceptable emulsions, solutions, suspensions, syrups and elixirs. In addition to the active compounds, the liquid dosage forms may contain inert diluents commonly used in the art, such solvents, solubilizing agents and emulsifiers.

Solid compositions of may also be employed as fillers in soft and hard-filled gelatin capsules using such excipients as lactose or milk sugar as well as high molecular weight polyethylene glycols, and the like.

When aqueous suspensions are used they can contain emulsifying agents or agents which facilitate suspension.

The oily phase of the emulsion pharmaceutical composition may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier that acts as a stabilizer. It is also preferred to include both an oil and a fat. Together, the emulsifier(s) with or without stabilizer(s) make up the emulsifying wax, and the way together with the oil and fat make up the emulsifying ointment base which forms the oily dispersed phase of the cream formulations.

If desired, the aqueous phase of the cream base may include, for example, a least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound that enhances absorption or penetration of the active ingredient through the skin or other affected areas.

The choice of suitable oils or fats for a formulation is based on achieving the desired cosmetic properties. Thus the cream should preferably be a non-greasy, non-staining and washable product with suitable consistency to avoid leakage from tubes or other containers. Straight or branched chain, mono- or dibasic alkyl esters such as di-isopropyl myristate, decyl oleate, isopropyl palpitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils can be used.

In practice, a compound/pharmaceutical compositions of the present invention may be administered in a suitable formulation to humans and animals by topical or systemic administration, including oral, inhalational, rectal, nasal, buccal, sublingual, vaginal, colonic, parenteral (including subcutaneous, intramuscular, intravenous, intradermal, intrathecal and epidural), intracisternal and intraperitoneal. It will be appreciated that the preferred route may vary with for example the condition of the recipient.

"Pharmaceutically acceptable dosage forms" refers to dosage forms of the compound of the invention, and includes, for example, tablets, dragees, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, Mack Publishing Co., Easton, Pa., latest edition.

"Formulations suitable for oral administration" may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tables may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compounds moistened with an inert liquid diluent. The tablets may optionally be coated or scored and may be formulated so as to provide slow or controlled release of the active ingredient therein.

Solid compositions for rectal administration include suppositories formulated in accordance with known methods and containing at least one compound of the invention.

If desired, and for more effective distribution, the compounds can be microencapsulated in, or attached to, a slow release or targeted delivery systems such as a biocompatible, biodegradable polymer matrices (e.g., poly(d, l-lactide coglycolide)), liposomes, and microspheres and subcutaneously or intramuscularly injected by a technique called subcutaneous or intramuscular depot to provide continuous slow release of the compound(s) for a period of 2 weeks or longer. The compounds may be sterilized, for example, by filtration through a bacteria retaining filter, or by incorporating sterilizing agents in the form of sterile solid compositions which can be dissolved in sterile water, or some other sterile injectable medium immediately before use.

"Formulations suitable for nasal or inhalational administration" means formulations which are in a form suitable to be administered nasally or by inhalation to a patient. The formulation may contain a carrier, in a powder form, having a particle size for example in the range 1 to 500 microns (including particle sizes in a range between 20 and 500 microns in increments of 5 microns such as 30 microns, 35 microns, etc.) Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents. Inhalational therapy is readily administered by metered dose inhalers.

"Formulations suitable for oral administration" means formulations which are in a form suitable to be administered orally to a patient. The formulations may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

"Formulations suitable for parenteral administration" means formulations that are in a form suitable to be administered parenterally to a patient. The formulations are sterile and include emulsions, suspensions, aqueous and non-aqueous injection solutions, which may contain suspending agents and thickening agents and anti-oxidants, buffers, bacteriostats and solutes which render the formulation isotonic, and have a suitably adjusted pH, with the blood of the intended recipient.

"Formulations suitable for rectal or vaginal administrations" means formulations that are in a form suitable to be administered rectally or vaginally to a patient. The formulation is preferably in the form of suppositories that can be prepared by mixing the compounds of this invention with suitable non-irritating excipients or carriers such as cocoa butter, polyethylene glycol or a suppository wax, which are solid at ordinary temperatures but liquid at body temperature and therefore, melt in the rectum or vaginal cavity and release the active component.

"Formulations suitable for systemic administration" means formulations that are in a form suitable to be administered systemically to a patient. The formulation is preferably administered by injection, including transmuscular, intravenous, intraperitoneal, and subcutaneous. For injection, the compounds of the invention are formulated in liquid solutions, preferably in physiologically compatible buffers such as Hank's solution or Ringer's solution. In addition, the compounds may be formulated in solid form and redissolved or suspended immediately prior to use. Lyophilized forms are also included. Systematic administration also can be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents may be used to facilitate permeation. Transmucosal administration may be through use of nasal sprays, for example, or suppositories. For oral administration, the compounds are formulated into conventional oral administration forms such as capsules, tablets, and tonics.

"Formulations suitable for topical administration" means formulations that are in a form suitable to be administered topically to a patient. The formulation may be presented as a topical ointment, salves, powders, sprays and inhalants, gels (water or alcohol based), creams, as is generally known in the art, or incorporated into a matrix base for application in a patch, which would allow a controlled release of compound through the transdermal barrier. When formulated in an ointment, the active ingredients may be employed with either a paraffinic or a water-miscible ointment base. Alternatively, the active ingredients may be formulated in a cream with an oil-in-water cream base. Formulations suitable for topical administration in the eye include eye drops wherein the active ingredient is dissolved or suspended in a suitable carrier, especially an aqueous solvent for the active ingredient. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

"Solid dosage form" means the dosage form of the compound of the invention is solid form, for example capsules, tablets, pills, powders, dragees or granules. In such solid-dosage forms, the compound of the invention is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, (i) lubricants, as for example, talc, calcium stearate, magnesium stearate, solid polyethylene glycols, sodium lauryl sulfate, (j) opacifying agents, (k) buffering agents, and agents which release the compound(s) of the invention in a certain part of the intestinal tract in a delayed manner.

Actual dosage levels of active ingredient in the compositions of the invention may be varied so as to obtain an amount of active ingredient that is effective to obtain a desired therapeutic response for a particular composition and method of administration for a patient. The selected dosage level therefore depends upon the desired therapeutic effect, on the route of administration, on the desired duration of treatment, the etiology and severity of the disease, the patient's condition and age, the potency of each component and other factors.

The method comprises administering to the animal an amount of a compound of any one of formulas I to IV which is effective for this purpose. In general, an effective amount of a compound of any of formulas I to IV is a dose between about 0.5 and about 100 mg/kg. A preferred dose is from about 1 to about 60 mg/kg of active compound. A typical daily dose for an adult human is from about 50 mg to about 5 g.

The percentage of active ingredient in a composition may be varied, though it should constitute a proportion such that a suitable dosage shall be obtained. Dosage unit compositions may contain such amounts of such submultiples thereof as may be used to make up the daily dose. Obviously, several unit dosage forms may be administered at about the same time. A dosage may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. It goes without saying that, for other patients, it will be necessary to prescribe not more than one or two doses per day. It will be understood, however, that the specific dose level for any particular patient will depend upon a variety of factors including the condition of the patient, the body weight, general health, sex, diet, time, duration and route of administration, rates of absorption and excretion, combination with other drugs and the severity of the particular disease being treated.

The formulations can be prepared in unit dosage form by any of the methods well known in the art of pharmacy. Such methods include the step of bringing into association the active ingredient with the carrier that constitutes one or more accessory ingredients. In general the formulations are prepared by uniformly and intimately bringing into association the active ingredient with liquid carriers or finely divided solid carriers or both, and then, if necessary, shaping the product.

The formulations may be presented in unit-dose or multi-dose containers, for example sealed ampoules and vials with elastomeric stoppers, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Compounds within the scope of the present invention exhibit marked pharmacological activities according to tests described in the literature and below, which tests results are believed to correlate to pharmacological activity in humans and other mammals.

We claim:
1. An N-monoacylated glycopeptide of formula IV

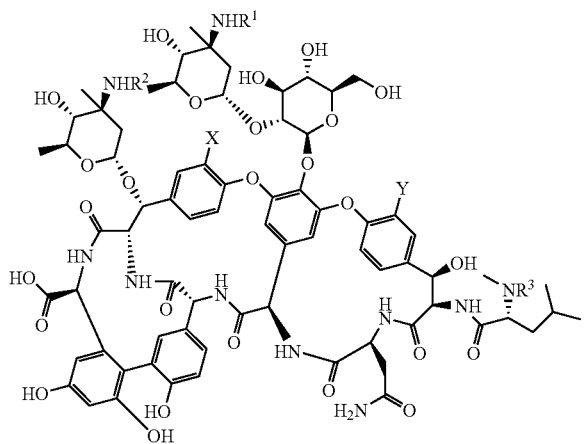

and pharmaceutically acceptable salts thereof;
wherein:
X and Y are independently hydrogen or chloro;
at least one of $R^1$, $R^2$, and $R^3$ is a group of formula Ia'

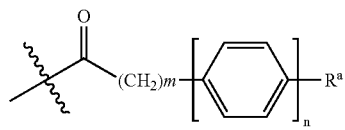

and $R^1$, $R^2$ and $R^3$ which are other than formula Ia are hydrogen;
m is an integer from 0 to 15;
n is 2;
and
$R^a$ is H, halo, $C_1$-$C_8$ alkyl, $C_1$-$C_8$ alkoxy, —$NH_2$, —NH($C_1$-$C_3$ alkyl) or —N(($C_1$-$C_3$)alkyl)$_2$.

2. The monoacylated glycopeptide of claim 1, wherein:
X and Y are independently hydrogen or chloro;
$R^1$ is a group of formula Ia'

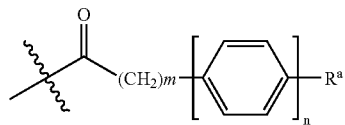

$R^2$ and $R^3$ are H;
m is an integer from 0 to 15;
n is 2; and
$R^a$ is H, halo, $C_1$-$C_8$ alkyl, $C_1$-$C_8$ alkoxy, —$NH_2$, —NH($C_1$-$C_3$ alkyl) or —N(($C_1$-$C_3$)alkyl)$_2$.

3. The monoacylated glycopeptide of claim 2, wherein X and Y are chloro, and $R^1$ is 4-(4'-chlorophenyl)benzoyl.

4. The monoacylated glycopeptide of claim 1, wherein:
X and Y are independently hydrogen or chloro;
R$^1$ and R$^3$ are hydrogen; R$^2$ is a group of formula Ia'

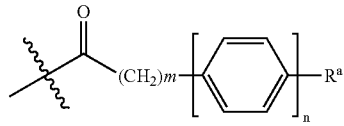

Ia' m is an integer from 0 to 15;
n is 2;
and
R$^a$ is H, halo, C$_1$-C$_8$ alkyl, C$_1$-C$_8$ alkoxy, —NH$_2$, —NH(C$_1$-C$_3$ alkyl) or —N((C$_1$-C$_3$)alkyl)$_2$.

5. The monoacylated glycopeptide of claim 1, wherein:
X and Y are independently hydrogen or chloro;
R$^1$ and R$^2$ are hydrogen; R$^3$ is a group of formula Ia'

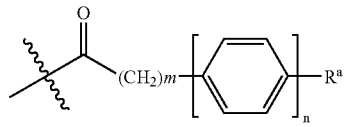

Ia' m is an integer from 0 to 15;
n is 2;
and
R$^a$ is H, halo, C$_1$-C$_8$ alkyl, C$_1$-C$_8$ alkoxy, —NH$_2$, —NH(C$_1$-C$_3$ alkyl) or —N((C$_1$-C$_3$)alkyl)$_2$.

6. The monoacylated glycopeptide of claim 1 wherein at least one of R$^1$, R$^2$, or R$^3$ is 4-phenylbenzoyl, or 4-(4'-chlorophenyl)benzoyl.

7. A pharmaceutical composition comprising an N-monoacylated glycopeptide as claimed in claim 1 and a pharmaceutically acceptable carrier.

8. A method of inhibiting growth of a microorganism, comprising providing a growth-controlling effective amount of an N-monoacylated glycopeptide of claim 1 to a locus where a microorganism susceptible to the antimicrobial activity of an N-monoacylated glycopeptide antibiotic of claim 1 is present, thereby inhibiting growth of a microorganism.

9. The method of claim 8, wherein said locus is in vivo or in vitro.

10. The method of claim 8, wherein said locus is an inert surface, a surface of a mammal, or a surface of a plant.

11. The method of claim 8, wherein said providing comprises applying or administering said glycopeptide antibiotic to said locus prior to, simultaneously with, or after contact of said microorganism with said locus.

12. A method of inhibiting growth of a microorganism, comprising contacting a microorganism susceptible to the antimicrobial activity of an N-monoacylated glycopeptide of claim 1 with a growth-controlling effective amount of an N-monoacylated glycopeptide antibiotic of claim 1, thereby inhibiting growth of a microorganism.

13. The method of claim 12, wherein said contacting is performed in vivo or in vitro.

14. A method for preparing an N-monoacylated glycopeptide of claim 1, comprising acylating the glycopeptide A82846A with an activated ester selected from N-acyl-hydroxysuccinimide and N-acyl-hydroxyphthalimide in dimethylsulfoxide to yield an N-monoacylated glycopeptide of claim 1.

15. A method of preparing an N-monoacylated glycopeptide of claim 1, comprising reacting the glycopeptide A82846A with an activated ester selected from N-acyl-hydroxysuccinimide and N-acyl-hydroxyphthalimide in aqueous methanol to yield an N-monoacylated glycopeptide of claim 1.

16. The method of claim 15, wherein said aqueous methanol comprises about 40% to about 60% water.

17. The method of claim 16, wherein said aqueous methanol comprises a mixture of about 1:1 methanol and water.

* * * * *

UNITED STATES PATENT AND TRADEMARK OFFICE
CERTIFICATE OF CORRECTION

PATENT NO. : 7,365,053 B2
APPLICATION NO. : 10/203533
DATED : April 29, 2008
INVENTOR(S) : Richard Craig Thompson et al.

It is certified that error appears in the above-identified patent and that said Letters Patent is hereby corrected as shown below:

The title is corrected to read as follows:

"SELECTIVE N-ACYLATION OF A82846 GLYCOPEPTIDE ANALOGS"

Column 1, lines 1 and 2, is corrected to read as follows:

"SELECTIVE N-ACYLATION OF A82846 GLYCOPEPTIDE ANALOGS"

Signed and Sealed this

Twenty-fifth Day of November, 2008

JON W. DUDAS
*Director of the United States Patent and Trademark Office*